United States Patent [19]

Colombo et al.

[11] 4,382,789
[45] May 10, 1983

[54] MANUAL PRESSURE SYRINGE FOR ODONTOLOGICAL USE

[75] Inventors: Domenico Colombo, Via Musa 4, Como, Italy; Americo Colombo, Como, Italy

[73] Assignee: Domenico Colombo, Como, Italy

[21] Appl. No.: 312,104

[22] Filed: Oct. 16, 1981

[30] Foreign Application Priority Data

Jan. 15, 1981 [IT] Italy ............................. 19138 A/81

[51] Int. Cl.³ ................................................ A61C 5/04
[52] U.S. Cl. ....................................... 433/89; 433/90; 222/391; 604/135
[58] Field of Search ............................. 433/81, 89, 90; 128/218 A, 218 F, 234, 237; 222/326, 386, 391

[56] References Cited

U.S. PATENT DOCUMENTS

| 2,643,655 | 6/1953 | McKay | 128/234 |
| 3,612,359 | 10/1971 | Sundholm | 222/326 |
| 4,072,254 | 2/1978 | Cox | 222/391 |
| 4,083,428 | 4/1978 | Ness | 222/326 |
| 4,339,058 | 7/1982 | Wendt | 222/326 |

FOREIGN PATENT DOCUMENTS

| 1171571 | 1/1959 | France | 128/218 F |
| 1456650 | 11/1976 | United Kingdom | 433/90 |

Primary Examiner—Robert Peshock
Assistant Examiner—John J. Wilson
Attorney, Agent, or Firm—Allison C. Collard; Thomas M. Galgano

[57] ABSTRACT

An improved manual pressure syringe for odontological use, includes a handgrip provided with a control lever, a barrel for a cartridge, and a bushing arranged on the longitudinal extension of the barrel. It also includes a shaft having a pushbutton at one end which is slidable in the bushing and acts on the piston of the cartridge, a thrust lever for the shaft operated by the control lever, and a coil spring arranged between the thrust lever and the bushing. The coil spring is formed of two end parts, the turns of which are of a larger diameter than that of the shaft, and an intermediate part, the turns of which are substantially of the same diameter as that of the shaft.

6 Claims, 3 Drawing Figures

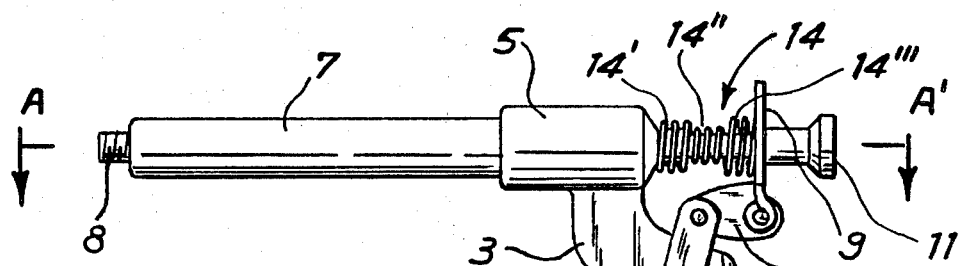
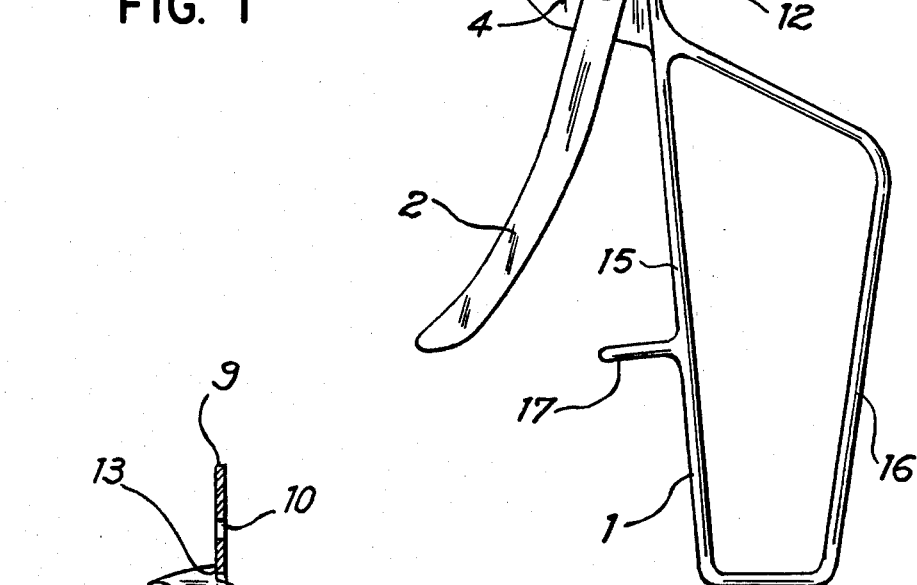
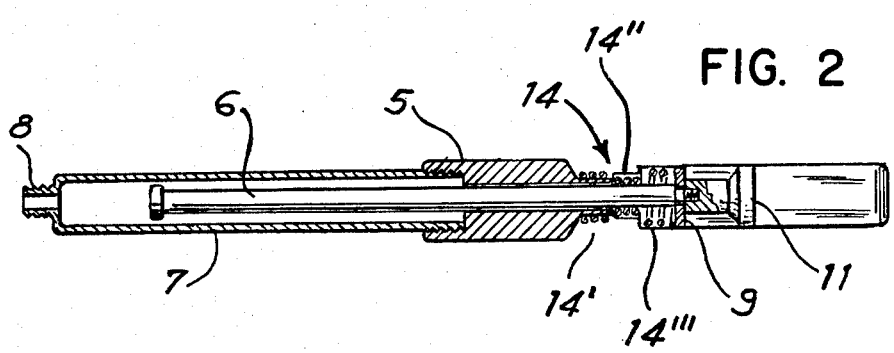

MANUAL PRESSURE SYRINGE FOR ODONTOLOGICAL USE

This invention relates to an improved, controlled manual pressure injection syringe for odontological use.

As it is well known, in order to ensure a painless operation in dentistry, an anesthetic solution is injected into the tissue between the tooth and the bone, technically referred to as the "periodontal membrane".

It is also well known that in order to obtain a good anesthesia, the anesthetic solution should reach the apex of each root of the tooth to be operated on, flowing along the root wall. Additionally, the tissue constituting the periodontal membrane exhibits some resistance to the liquid diffusion and this resistance would vary depending on the state of said tissue which, in turn, would also depend on the patient's age. Therefore, in order to provide satisfactory results, it is necessary that the injection be carried out in a gradual and continuous manner, to continuously match the pressure within the vial-tube with that within the periodontal membrane, so as to avoid sudden changes in pressure.

To effect injections in the periodonatal membrane, different types of injection syringes are known. However, such known syringes, while affording acceptable results, do not afford all of the required requisites for a perfect anesthesia of the dental tissue.

As it is well known, an injection syringe generally comprises a handgrip provided with a control lever, sealing means for a container of the cartridge, a shaft sliding longitudinally of the barrel in a bushing arranged on the longitudinal extension of the barrel, and acting on the cartridge piston, and thrust lever means operated by the control lever, which operate on the shaft moving the latter in a longitudinal direction.

After pressure release on the control lever, a plurality of springs serve to move back to and maintain at rest position, the shaft, the control lever and the thrust lever. Moreover, a further generally C-shaped spring is effective via retaining means on the sliding surface of the shaft, frictionally locking the latter at its advanced position as the control lever is released.

The connection between the thrust lever and shaft is generally accomplished by providing the shaft with grooves or transverse rings or evenly spaced apart threads on its surface and providing the thrust lever with a throughbore of a larger diameter than that of the shaft and having the free end of said shaft slipped therethrough.

The particular configuration of the above described shaft involves a series of disadvantages, such as an undesired noise of movement, a discontinuity of sliding, the need of exerting a higher pressure than that required to overcome the membrane resistance, etc. Another disadvantage of such known syringes is that where any anesthetic solution should discharge from the cartridge, it deposits on the retaining means acting on the shaft surface, rendering its locking function on said shaft at its advanced position impossible.

It is therefore the object of the present invention to provide an improved controlled manual pressure injection syringe for odontological use, not having the aforementioned disadvantages.

More particularly it is the object of the present invention to provide an improved syringe, wherein the sliding of the shaft is smooth, continuous, controllable and noiseless, and the sliding of the thrust lever on the shaft in the return step at the beginning of the stroke is noiseless.

It is a further object of the present invention to provide an improved syringe which enables the continuous and gradual adjustment of the pressure within the cartridge in relation to the resistance exhibited by the periodontal membrane.

According to the present invention, these and other objects are accomplished by a syringe for odontological use, compising a handgrip provided with a control lever, a barrel for the cartridge, a bushing arranged on the longitudinal extension of the barrel and to which the latter is connected, a shaft having a smooth surface, sliding in the bushing for longitudinal movement relative to the barrel and acting on the cartridge piston, a thrust lever for the shaft operated by the control lever, and a coil spring forced on the end rear part of the bushing, arranged between the thrust lever and the bushing. The coil spring is formed of two end parts, the turns of which are of larger diameter than that of the shaft, and an intermediate part, the turns of which are substantially of the same diameter as that of the shaft.

The arrangement and particular structure of the spring according to the present invention enables such a spring to perform all of the functions which in previously known syringes have been performed by a plurality of resilient means. Particularly, the rear portion of the spring, that is the portion contacting the thrust lever, performs the function of keeping the lever in continuous contact with the shaft surface in order to obviate any clearance between the thrust lever and the shaft, and also to move the control lever back to its initial stroke position. The intermediate part, the turns of which are of less diameter than that of the other turns and frictionally engage on the shaft surface, performs the shaft locking function after release of the control lever, normally at the end of the stroke thereof, while the front part of the spring, that is the part screwed on the bushing, performs the function of maintaining the intermediate and the rear part of the spring at the optimum positions of respective operation. The smooth surface of the shaft enables an optimum and noiseless sliding both in the bushing and during the return movement of the thrust lever.

The constructive and functional characteristics of the present improved syringe for odontological use will be more clearly understood from the following description, in which reference is made to the figures of the accompanying drawing, showing a preferred exemplary but unrestrictive embodiment of the present invention, and in which:

FIG. 1 is a schematic perspective view of the injection syringe according to the present invention;

FIG. 2 is a schematic cross-sectional view of the injection syringe, taken through line A-A' of FIG. 1; and FIG. 3 is a fragmentarily-illustrated schematic view of the lever system for the control of the thrust lever.

Referring now in detail to the figures of the accompanying drawing, an improved injection syringe according to the present invention comprises a handgrip 1 provided with a control lever 2 pivotably mounted on a support 3 via a pin 4 which support 3 is integral with said handgrip.

A longitudinal bushing 5 is secured to support 3 and has a shaft 6 mounted thereon in a longitudinally-slidable manner having a pushbutton 11 at one end thereof. The front part of bushing 5 and the longitudinal extension thereof has secured thereto by bayonet or threaded fitting a cartridge barrel 7 provided at its free end with a connection 8 for a needle attachment. The front free end of shaft 6 acts upon the piston of the cartridge arranged in said barrel 7. A thrust lever 9, which is provided with a hole 10 of a slightly larger diameter than that of shaft 6 which passes through the hole, is mounted on shaft 6.

A link 12, provided with a hole at each end and a projection or abutment surface 13, connects the end of thrust lever 9 to the free end of control lever 2.

By pressing the thrust lever 9 by means of one's finger on projection 13 at a substantially vertical position, the shaft 6 can be moved back by one's other hand to its initial or starting stroke position. Therefore, projection 13 is the reference location for releasing the thrust lever 9 from shaft 6.

A coil spring 14 is biasly arranged on bushing 5 between the rear end of bushing 5 and thrust lever 9.

Coil spring 14 is formed of three parts 14', 14'' and 14''', of which the two end parts 14' and 14''' comprise turns of larger diameter than that of shaft 6, and the intermediate part 14'' turns of substantially the same diameter as that of shaft 6, so as to frictionally engage the smooth surface of said shaft 6. The rear part 14''' of spring 14 performs the function of maintaining the surface of shaft 6 in continuous contact with the thrust lever 9 in order to obviate any clearance between said thrust lever 9 and shaft 6, and to move control lever 2 back to the stroke starting position.

The intermediate part 14'' of spring 14, the turns of which are of less diameter than the other turns and frictionally engage on the surface of shaft 6, performs the locking function for shaft 6 after release of control lever 2, normally at the end of the stroke thereof; whereas the front part 14' of the spring or the part screwed on the bushing, performs the function of holding the intermediate part 14'' and the rear part 14''' of the spring at the optimum positions of respective operation.

Handgrip 1 comprises two parts 15 and 16, of which the part adjacent to control lever 2 is provided with a spur 17 acting as a stop for the end of the stroke for control lever 2 and under which spur two fingers of the operator's hand can be accommodated. The outer part 16, preferably substantially parallel to control lever 2 at rest position, has the purpose of offering the maximum stability of gripping by the hand on the handgrip 1 during the pressure on control lever 2.

The operation of the above described injection syringe for odontological use is as follows.

Shaft 6 is retracted throughout its length by acting on the pushbutton 11 and causing it to slide in hole 10 of thrust lever 9. At this position, barrel 7 containing the cartridge can be secured to bushing 5. The needle is screwed to connection 8 of barrel 7. Thus, the syringe is ready for use.

By pulling control lever 2 rearwardly, shaft 6 is gradually urged forwardly through the action of thrust lever 9.

The front free end of shaft 6 acts upon the piston of the cartridge in the barrel 7, effecting the anesthetic injection. Each pressure movement on the control lever 2 causes a corresponding forward longitudinal movement of shaft 6. At substantially vertical postion, thrust lever 9 is maintained in continuous contact with the shaft 6 by the action of spring part 14''', as previously described. Thus, any clearance between thrust lever 9, shaft 6, link 12 and control lever 2 is eliminated. Therefore, the anesthetic solution dose injected upon pressing control lever 2, from the start to the end of the stroke, is always constant.

After release of control lever 2, the latter is brought back to its rest or initial stroke or starting position by release of the finger grip and the action of spring part 14'''.

When the cartridge piston reaches the front end of its stroke, button 11 presses on thrust lever 9, whereby the latter is rendered ineffective or inoperative. Now, control lever 2 idly operates. This allows the operator to recognize that the cartridge is completely emptied and, to avoid useless pressing on the lever, instead of erroneously thinking that it is caused by an increased resistance by the tissues due to a casual displacement of the needle. The injection operation is now terminated. To bring shaft 6 back to the stroke starting position to recharge the syringe with a new cartridge, the previous procedure must be followed, that is to urge thrust lever 9 forward against projection 13 and at the same time exert a rearward pull on shaft 6 by gripping it on button 11.

From the foregoing, the simplicity in construction and use and the functionality of the injection syringe according to the present invention is believed apparent. Changes, modifications and variants may be made to the practical embodiment of the present manual pressure syringe for odontological use within the spirit of the present invention and without departing from its covering scope.

What is claimed is:

1. A manual pressure syringe for odontological use, comprising:
    a handgrip having a movable control lever coupled thereto;
    a bushing coupled to said handgrip;
    a tubular barrel coupled to said bushing for a cartridge having a movable piston;
    a shaft having a smooth surface which is slidably mounted in said bushing for longitudinally-reciprocable movement within said barrel, and for acting upon a cartridge piston;
    a thrust lever for effecting movement of said shaft operated by said control lever; and
    a coil spring arranged between said thrust lever and bushing, comprising two end parts, the turns of which are of larger diameter than that of said shaft, and an intermediate part, the turns of which are of substantially the same diameter as that of said shaft.

2. The syringe according to claim 1, wherein said thrust lever is provided with a hole of a diameter slightly larger than that of said shaft, the latter being received through said hole.

3. The syringe according to claim 1, wherein said thrust lever and said control lever are coupled to one another by means of a link pivoted at its two ends to said levers.

4. The syringe according to claim 3 wherein said link is provided with a projection which serves as an abutment.

5. The syringe according to claim 1, wherein said handgrip is formed of two parts, a rear part which is substantially parallel to said control lever in rest position, and a front part disposed adjacent to the control lever which is provided with a forward-projecting spur for engagement with said control lever.

6. A trigger mechanism for a manual pressure syringe for odontological use, comprising:

a bushing;

a shaft slidably mounted in said bushing for longitudinal reciprocal movement and having a pushbutton member at a rear end thereof;

a thrust lever mounted on said shaft and disposed between said bushing and said pushbutton member;

a coil spring mounted on said shaft and arranged between said thrust lever and said bushing, and comprising two end parts, the turns of which are of larger diameter than that of said shaft, and an intermediate part, the turns of which are of substantially the same diameter as that of said shaft.

* * * * *